United States Patent
Spahn (10) Patent No.: US 8,165,360 B2
(45) Date of Patent: Apr. 24, 2012

(54) X-RAY IDENTIFICATION OF INTERVENTIONAL TOOLS

(75) Inventor: Martin Spahn, Chicago, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1127 days.

(21) Appl. No.: 11/681,865

(22) Filed: Mar. 5, 2007

(65) Prior Publication Data
US 2008/0137923 A1 Jun. 12, 2008

Related U.S. Application Data

(60) Provisional application No. 60/868,770, filed on Dec. 6, 2006.

(51) Int. Cl.
*G06K 9/00* (2006.01)
*G06K 9/40* (2006.01)

(52) U.S. Cl. ........................ 382/128; 382/254

(58) Field of Classification Search .................. None
See application file for complete search history.

(56) References Cited

U.S. PATENT DOCUMENTS

| | | | |
|---|---|---|---|
| 5,959,300 A | 9/1999 | Hines et al. | |
| 6,349,373 B2 | 2/2002 | Sitka et al. | |
| 6,520,912 B1 | 2/2003 | Brooks et al. | |
| 6,697,664 B2 * | 2/2004 | Kienzle, III et al. | 600/427 |
| 7,022,073 B2 | 4/2006 | Fan et al. | |
| 7,043,064 B2 | 5/2006 | Paik et al. | |
| 7,289,652 B2 * | 10/2007 | Florent et al. | 382/130 |
| 2005/0099416 A1 * | 5/2005 | Moreau-Gobard et al. | 345/419 |
| 2006/0093193 A1 * | 5/2006 | Viswanathan | 382/128 |
| 2007/0242794 A1 * | 10/2007 | Stanton et al. | 378/5 |
| 2008/0045827 A1 * | 2/2008 | Rongen et al. | 600/407 |
| 2008/0118115 A1 * | 5/2008 | Williamson | 382/128 |
| 2008/0292194 A1 * | 11/2008 | Schmidt et al. | 382/217 |

OTHER PUBLICATIONS

Aufrichtig, R.; Wilson, D.L.; , "X-ray fluoroscopy spatio-temporal filtering with object detection," Medical Imaging, IEEE Transactions on , vol. 14, No. 4, pp. 733-746, Dec. 1995.*

* cited by examiner

*Primary Examiner* — Stephen R Koziol
*Assistant Examiner* — Nirav G Patel
(74) *Attorney, Agent, or Firm* — Alexander J Burke (57) ABSTRACT

A system and method enhance the visibility of medical devices shown in internal images. A medical device may be inserted into a patient. Internal images of the patient may then be acquired via various medical imaging techniques. However, the medical device may only be partially visible in the images, if at all. For instance, the images may be acquired with minimal radiation exposure to the patient and/or the medical device may be thin or made of translucent material. Model data may be associated with the geometry or other characteristics of the medical device. The model data may be adapted, such as rotated, resized, bent, or otherwise modified, to form a "best fit" with the medical device as actually shown in the internal images. The adapted model data may be superimposed onto a display of the medical device as shown in the internal images to enhance visibility of the medical device.

24 Claims, 4 Drawing Sheets

X-RAY IDENTIFICATION OF INTERVENTIONAL TOOLS

PRIORITY AND CROSS-REFERENCE TO RELATED APPLICATION

This application claims priority under 35 U.S.C. §119(e) to provisional application Ser. No. 60/868,770, filed on Dec. 6, 2006 and entitled "Stent Paint," which is incorporated by reference in its entirety herein.

BACKGROUND

The present embodiments relate generally to medical imaging. In particular, the present embodiments relate to enhancing the visibility of medical instruments shown within medical images.

In general, interventional or cardiac angiography examinations involve the deployment of stents into clotted vessels after the reopening of a stenosis, such as via a ballooning or other procedure. It is crucial that the interventional physician be able to see the stent during and after deployment to judge correct positioning, opening, and other movement of the stent within the patient.

Typical methods by which internal medical images are acquired may involve exposing the patient to radiation. As a result, conventional imaging methods may be associated with the tendency to acquire images using a small dose of radiation. However, as the stent material may be relatively thin and translucent, visualization of the stent using a limited dose of radiation and/or with conventional techniques may be problematic.

BRIEF SUMMARY

By way of introduction, the embodiments described below include methods, processes, apparatuses, instructions, or systems for enhancing the visibility of medical devices shown within medical images. Medical devices may be inserted into a patient during a medical procedure. Medical image data corresponding to internal images of the patient may be acquired during or after the procedure. The image (or image data) of the medical device that is being displayed may be altered to enhance its visibility. For instance, the medical device may be associated with model data, the model data being based upon an identification of the medical device, such as by type or characteristic. The model data may be matched with the image data, or a portion thereof, using a best fit or other algorithm. The model or image data may be manipulated to add more detail or otherwise enhance the visibility of the medical device as shown in the image and/or represented by corresponding image data.

In a first aspect, a method provides automatic image enhancement. The method includes acquiring an image of a medical device internal to a patient and enhancing visibility of the medical device as shown in the image as a function of model data associated with the medical device.

In a second aspect, a method provides automatic image enhancement. The method includes identifying a medical device and acquiring model data associated with the medical device based upon the identification. The method also includes acquiring an image of the medical device within a patient and enhancing visibility of the medical device as shown in the image as a function of the model data to alter a display of the image.

In a third aspect, a data processing system provides automatic image enhancement. The system includes means for acquiring an image of a medical device within a patient and a processor operable to alter a display of the image based upon an identification of the medical device such that visibility of the medical device as shown on the display is enhanced.

In a fourth aspect, a computer-readable medium having instructions executable on a computer is described. The instructions include fitting a virtual medical device onto a corresponding actual medical device shown in an internal image of the actual medical device, and enhancing visibility of the actual medical device as shown on a display is enhanced.

The present invention is defined by the claims set forth herein. Nothing in this section should be taken as a limitation on those claims. Further aspects and advantages of the invention are discussed below in conjunction with the preferred embodiments and may be later claimed independently or in combination.

DESCRIPTION OF THE DRAWINGS

The present embodiments will become more fully understood from the detailed description given herein below and the accompanying drawings which are given by way of illustration only, and are not limitative of the present invention, and wherein.

DETAILED DESCRIPTION OF THE DRAWINGS AND EXEMPLARY EMBODIMENTS

The embodiments described herein include methods, processes, apparatuses, instructions, or systems for automatic image enhancement. The image enhancement may include enhancing the visibility of a medical device displayed in medical image(s) internal to a patient. The image enhancement also may include simultaneously enhancing the visibility of bodily structure(s) in which the medical device is inserted.

Medical procedures may entail the insertion of medical instruments, objects, or other devices into a patient. For instance, cardiac angiography or other interventional procedures may involve the insertion of interventional tools and objects, such as stents, catheters, balloon catheters, wires, needles, cameras, and other medical devices, into a patient. During the procedures, medical image data associated with internal images of the patient may be acquired using various medical imaging means and techniques. The visibility of a medical device shown in the internal images acquired may be enhanced by matching the images or corresponding imaging data with adapted model data associated with the medical device, such as by using a best fit algorithm or other technique.

As an example, the visualization of a stent partially shown in acquired internal images may be enhanced. Stents may be manufactured from translucent material that provides little absorption of x-ray radiation, or other medical imaging energy. Additionally, in a moving environment, such as within a beating heart or a blood vessel, stents may be very hard to see or become blurry.

The embodiments discussed herein may enhance the visibility of the stent as shown in the images acquired by making use of the knowledge of the design and structure of the particular stent being used. The known characteristics of the stent may be used to create model data that defines or represents the stent. The model data that virtually models the stent may be altered to "match" or "line up with" the imaging data associated with the portion of the images in which the stent is displayed. After which, the matched model data may be used to outline, fill-in, or otherwise improve the detail of the stent as shown in the images.

The visibility of other medical devices may be enhanced as well. For example, wires, cameras, manipulating devices on wire, "submarine type cameras" that travel within vessels, catheters, needles, and other small and/or translucent devices that are difficult to x-ray image may have their visibility enhanced by the embodiments discussed herein.

In general, the process of enhancing medical device visibility may include identifying the type of medical device to be delivered to a position within a patient and/or seen in an internal image sequence. A medical imaging system may download a two-dimensional, a three-dimensional, or other model of the medical device. The model may include various geometric parameters associated with the medical device. For instance, in one embodiment, the medical device is a stent. As such, the model may include the length, the width, the position of struts, type of material, and other parameters for either or both the non-expanded and the expanded stent. Other geometric or imageable parameters may be used.

The type of medical device may be identified via a user selection from a pulldown or other menu, a voice recognition means, a barcode reader, or other input means. Alternatively, the specific type of medical device may be automatically identified by a processor analyzing the image data.

Image data may be acquired via various medical imaging modes, such as imaging systems that employ x-ray imaging techniques. Subsequently, geometric data associated with the acquisition of the image(s) may be obtained. The geometric data may include source-to-imager distance (SID), an estimate of the medical device-to-x-ray detector distance, magnification settings, detector pixel size, or other geometric data. The geometric data may be used to calculate the expected size and/or orientation of the medical device in the image (in a given projection). X-ray parameters, such as generator voltage (kV), filtration, and angulation settings/parameters, as well as patient characteristics, including patient weight, size, or belly circumference, may be acquired to further develop a guesstimate of what the medical device should look like in the images acquired.

An optional step in the process may involve providing a coarse position of the medical device within the images. For instance, a mouse click upon a portion of an individual image or a user touching a portion of a touch display screen showing the image may identify a localized area of the image in which the medical device is located. The medical device also may be identified as either non-expanded or expanded, such as via a voice recognition system, a mouse, a keyboard, or other technique. Alternatively, determining a localized area of interest in which the medical device resides may be omitted or performed automatically.

The model medical device, such as either an expanded or un-expanded stent, may be fitted to the actual image. The fitting process may account for the expected contrast of the imaged medical device, the actual acquisition parameters, such as x-ray voltage (kV) or dose, and the patient characteristics (such as weight, size, and belly circumference). For example, the model may be fitted to the actual device using the model geometric data adapted for size and acquisition parameters. Fitting the model to the actual device also may use patient weight and other characteristics to estimate the expected level of contrast of the medical device within the image if a contrast agent is employed. The fit procedure may include rotating, translating, resizing, warping, and/or bending the model medical device to get a best fit of the model to the actual image(s). The model is fit by correlation, minimum sum of absolute differences or other fitting algorithm. Any search pattern may be used. Exemplary fit procedures may include elastic registration techniques, registration techniques that use grid-based warp functions, non-rigid registration techniques that employ statistical deformation models, or other techniques.

As noted, the model or virtual medical device may be adjusted (bent, rotated, resized, or otherwise modified) to best fit the actual medical device as shown in the image data. The model medical device may be drawn onto the x-ray image, such as by using gray shades or color, to improve the visibility of the actual device's relative location to anatomical structures in particular vessels. Using a bi-planar medical imaging means in which the medical device is imaged from two or more different angles may improve the accuracy of the resultant enhanced images. For instance, using multiple angles may strongly improve the fit procedure, as better information about the rotation, bending, and apparent size of the actual medical device inside of the patient is acquired.

I. Exemplary Methods

Figure 1:
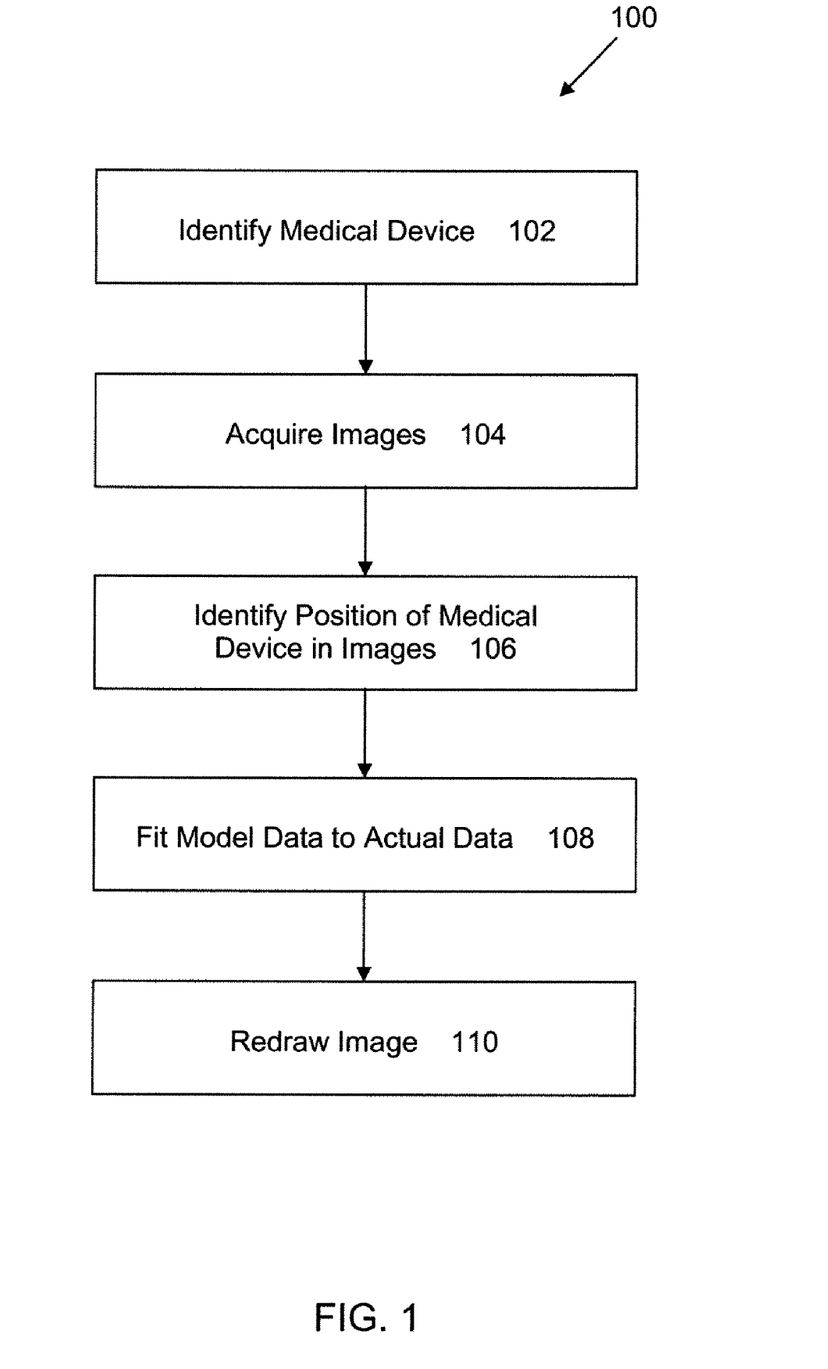
FIG. 1 illustrates an exemplary method of enhancing the visibility of a medical device as shown in a medical image.

FIG. 1 illustrates an exemplary method of enhancing the visibility of a medical device shown in a medical image 100. The method 100 may include identifying a medical device 102, acquiring internal images 104, identifying the location of the medical device in the internal images 106, fitting model data to actual image data 108, and redrawing the image 110. The method may include additional, fewer, or alternate actions. For example, acts 106 and 108 are performed as a single act. Identifying the best fit also identifies the location.

The method 100 may identify a medical device 102. A medical device used during an interventional medical procedure may be identified before or during the medical procedure. The medical device may be identified by type of device, such as stent, catheter, needle, wire, camera, or other medical device. The medical device may be identified by model type, such as by part or model number. Alternatively, the medical device may be identified by operational use or other characteristics. For example, a stent may be identified as currently being either expanded or non-expanded, and a catheter may be identified as a balloon catheter. Other identifications may be used.

The method 100 may acquire internal images of a patient 104. Various imaging devices and techniques may be employed to acquire the images and associated imaging data that defines the images. In one embodiment, the entire method 100 may be mapped onto software that runs on an image acquisition workstation or a review imaging system. The medical imaging device for acquiring images of a medical device within a patient may include x-ray, MRI (magnetic resonance imaging), CT (computed tomography), ultrasound, PET (positron emission tomography), or other radiation related medical imaging devices.

The method 100 may identify the position of the medical device in the images 106. For instance, a user may click upon a portion of a display using a mouse or touch a portion of a touch screen in which the medical device is shown. As a result, a localized portion of the display, i.e., an area of interest, may be identified as having been selected by the user for analysis. Alternatively, a localized portion of the image in which the medical device is located may be automatically determined by processing the image data. Determining an area of interest within the image to analyze, as compared to the entire image, may create computing efficiencies. For example, processing capabilities may not need to be expended analyzing portions of images unrelated to the medical device and for which no visibility enhancement is necessary. If a best fit algorithm is employed to adapt model data to match the image data associated with the actual device as discussed herein, the algorithm need only analyze the area of interest within the image(s) selected. Hence, selecting an area of interest may minimize the amount of work required by the fitting procedure.

The method 100 may adapt the model data associated with the medical device to fit the image data corresponding to the medical device 108. The model data may be envisioned as representing a virtual medical device. The model data may include various geometric dimensions of the actual medical device used during the medical procedure and shown in the images. Accordingly, the knowledge of the physical parameters of the medical device that is only partially or vaguely shown in the images may be used to further or fully develop how the medical device looks in the images as displayed. The relative orientation, scale, and image plane cross-section may be used for better fitting.

Mathematical operations may be performed on the model data to alter the size and shape of the virtual medical device represented by the model data to match, or "fit" onto, the actual medical device as shown in the images/image data. For example, a best fit algorithm may be employed that adjusts the model data and/or corresponding virtual medical device representation to create adjusted model data that fits the geometric shape of the actual medical device imaged. In one embodiment, once the device is located by translation and/or rotation, the best fit based on a scale search may be used. The adjusted model data may then be superimposed onto the image of the actual medical device to enhance the detail of the actual medical device as shown in the image.

Various types of best fit algorithms may be employed to match the model data with the images/image data of the actual medical device. In one embodiment, a chi-squared algorithm may be employed. The algorithm may use linear or non-linear regression to fit the model data to the actual medical device image. Alternate best fit algorithms may be used. For instance, U.S. Pat. Nos. 7,043,064, 5,959,300, 7,022,073, and 6,520,912, which are all incorporated by reference herein in their entireties, disclose best fit algorithms and methods associated with medical images. Other mathematical operations may be performed to adapt the model data.

The method 100 also may optionally employ organ model data that models a human organ. For instance, if one knows which artery in which a stent is to be placed and the specific type of stent to be deployed, that knowledge provides a good initial estimate of what the actual stent should look like once actually deployed within the patient. Angulation parameters associated with the imaging device may be used to further define an initial orientation of the stent within the patient.

The organ model data may be stored in a memory unit. The organ model data may represent a virtual bodily structure or a portion thereof. For example, the organ model data may represent a vessel or a vessel tree, including a branch in a vessel. Alternatively, the organ model data may represent the heart or an artery of the heart. As human hearts are typically very similar in shape from person to person with relatively similar characteristics (such as age and weight), relatively accurate modeling may be possible. Other bodily structures may be modeled. Before or during an interventional procedure, the type of bodily structure or portion thereof that is intended to be or currently being imaged may be identified manually by the user or automatically by a processor analyzing the images acquired.

Similar to the model data associated with the medical devices, the organ model data may be fit onto the actual organ as shown in the images displayed to enhance the visibility of the organ. In other words, both the visibility of a medical device and an organ may be simultaneously enhanced using respective model data. The organ model data which represents a virtual bodily structure may be fitted onto the actual bodily structure as shown in the images, similar to the manner in which the virtual medical device is adapted to fit the actual medical device. The same or a different best fit algorithm may be employed to fit the virtual bodily structure onto the actual bodily structure, such as by stretching, shrinking, moving, and/or rotating the virtual bodily structure to match up with the image of the actual bodily structure.

The method 100 may update a display of the internal images 110. The images may be updated by superimposing the adapted model data upon the portion of the image showing the actual medical device. By redrawing the image with the adapted model data drawn on top of a faint image of the corresponding medical device, the visibility of the medical device as shown in the images may be enhanced. The model data may represent color, gray scale, shading, opacity, or other information to further distinguish the device in the image. Alternatively, the identified image data is highlighted, such as by colorization or adjustment of intensity.

Likewise, the images may further be updated by superimposing the adapted organ model data upon the portion of the image showing the actual bodily structure. By redrawing the image with the adapted organ model data drawn on top of a faint image of the corresponding bodily structure, the visibility of the bodily structure may be enhanced. Enhancing the visibility of both the medical device and the organ in which the medical device is located may facilitate the ease of understanding by medical personnel of the actual orientation of the medical device with respect to the organ and the patient.

Figure 2:
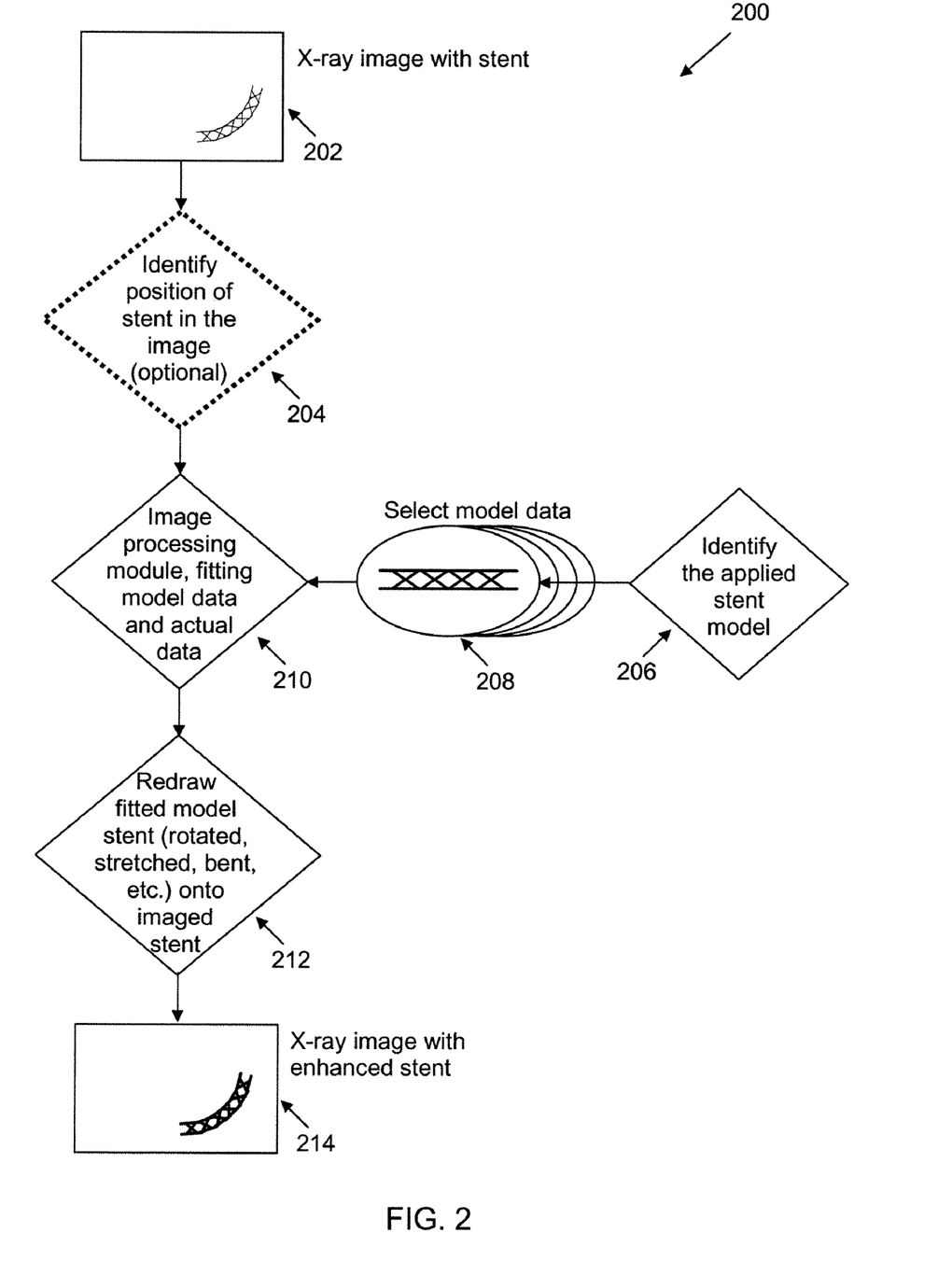
FIG. 2 illustrates an exemplary method of enhancing an internal image of a stent.

In one embodiment, the method may enhance the visibility of a stent internal to a patient. FIG. 2 illustrates an exemplary method of enhancing an x-ray image of a stent 200. The method 200 may include acquiring an x-ray image that includes a stent 202, identifying the position of the stent within the image 204, identifying the applied stent model 206, selecting model data 208, fitting model data to actual data 210, redrawing the fitted model stent onto the imaged stent 210, and displaying the x-ray image(s) with the stent image being visually enhanced 212. The method may include additional, fewer, or alternate actions.

The method may include acquiring an x-ray image of a stent 202. As shown in FIG. 2, during use, the stent may become bent, such as to accommodate the structure of a blood vessel, heart artery, or other bodily structure. The x-ray image of the stent may be faint or only partially displayed in an internal image. As indicated in FIG. 2, the method may optionally include identifying the position of the stent within the image 204, as discussed herein.

The method may identify, either manually or automatically, the applied stent model 206. For example, different models are matched to the image data and the model with the best fit is identified. Using the identification of the stent model, a corresponding stent model data set may be selected from a number of stent model data sets 208. For example, a number of stent model data sets may be stored in and accessible from a memory unit.

The stent model data set selected may be used by an image processing module residing on a processing unit. The image processing module may fit the model data with the actual image data associated with the x-ray image of the stent 210. The model stent may be redrawn to be rotated, stretched, shrunk, bent, or otherwise altered to fit the imaged stent. In one embodiment, the method may use a best fit or other algorithm to fit the model stent onto the actual stent as shown in the images. For instance, a mathematical optimization technique may use linear or non-linear regression equations, such as ordinary least squares or polynominal equations.

Subsequently, the fitted model stent may be drawn onto the imaged stent 212 or the imaged stent 212 altered. The resulting image displayed may show the x-ray image with the image of the stent being improved 214 and showing more detail of the structure of the stent. As indicated by FIG. 2, the stent displayed in the redrawn x-ray image is more clearly visible as compared to the original image displayed.

II. Exemplary Imaging System

Figure 3:
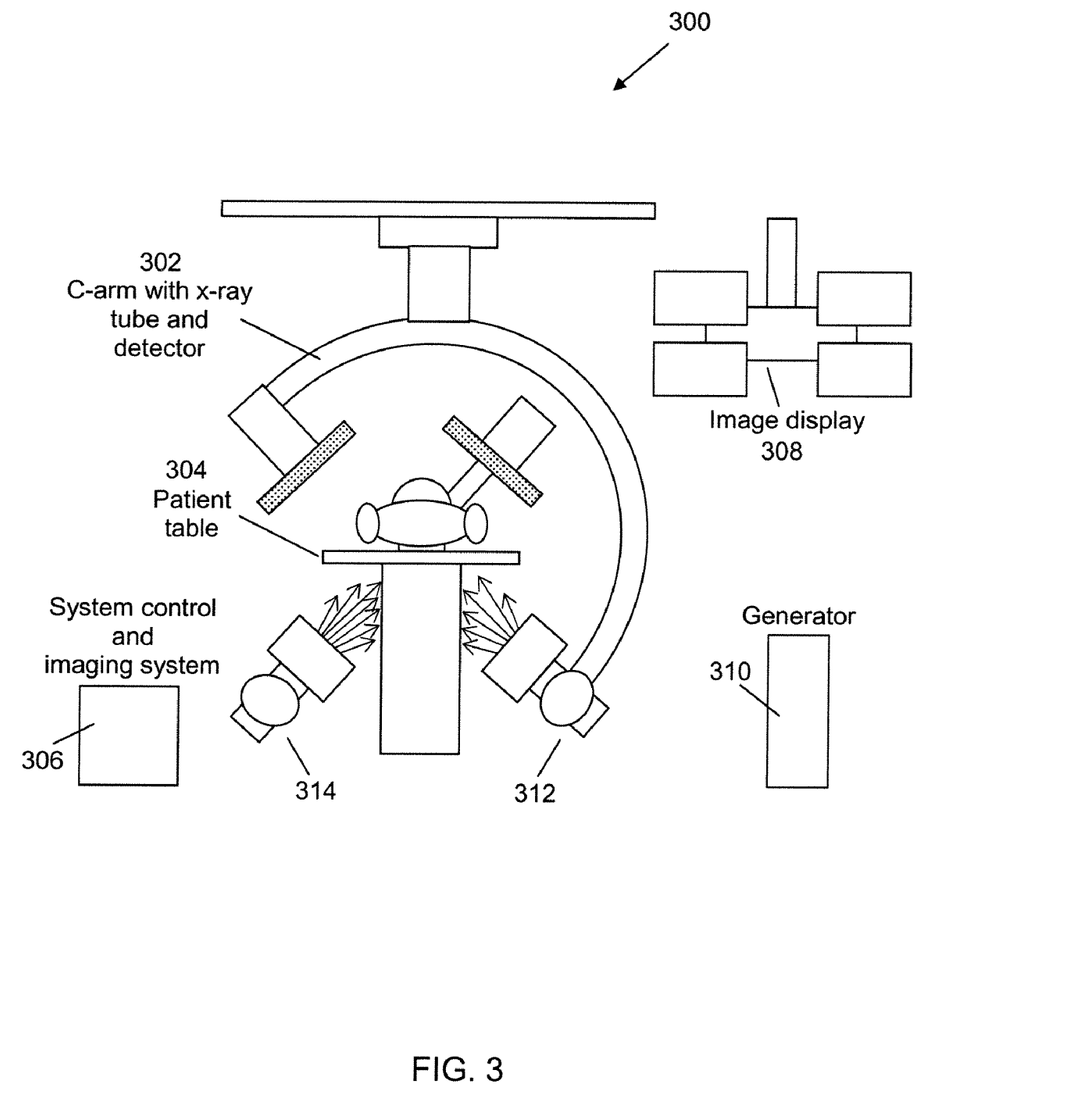
FIG. 3 illustrates an exemplary medical imaging system.

The method and system for enhancing the visibility of medical devices in internal images may involve the use of an imaging system. FIG. 3 illustrates an exemplary x-ray imaging system 300. The x-ray imaging system 300 may include a C-arm imaging device 302, a patient table 304, a system controller 306, an image display 308, and a voltage generator 310. The imaging system may include additional, fewer, or alternative components.

The C-arm imaging device 302 may include one or more C-arms, each C-arm having an x-ray tube or source on one end and a detector on the other end. The C-arm may be operational to acquire images at different angles. In one embodiment, the C-arm imaging device 302 is configured to be a bi-planar device having two C-arms 312, 314 operable to acquire images simultaneously. By acquiring internal images from two different views at the same time, better composite images may be generated. The images acquired may be either two-dimensional or three-dimensional.

In one aspect, the images are intended to be acquired during an interventional procedure and adjusted in real-time or nearly real-time, i.e., during the procedure. The images may be updated to enhance the visibility of the medical device while the patient is still lying on the patient table 304.

Alternatively, the image enhancement may be used for diagnostic purposes and non-interventional procedures. For instance, the image enhancement embodiments as discussed herein may be used to enhance the visibility of medical devices previously deployed within a patient, such as stents. In one aspect, the non-interventional procedures may acquire internal images of the medical device within the patient after a contrast medium has been injected into the patient. The enhancement of the visibility of a medical device during a non-interventional procedure may help medical personnel determine if a currently deployed medical device is still working as intended, such as if a blood vessel remains sufficiently open.

The system controller 306 may control the operation of the medical image system during use. The system controller 306 may be a workstation, computer, processor, or other controller. The system controller 306 may be operable to direct that the images acquired be displayed on an image display 308. The image display may include one or more display screens. A voltage generator 310 may generate a voltage required by the x-ray imaging system 300. The voltage may be used as an input parameter to estimate what the acquired images of the medical device should look like.

III. Exemplary Data Processor

Figure 4:
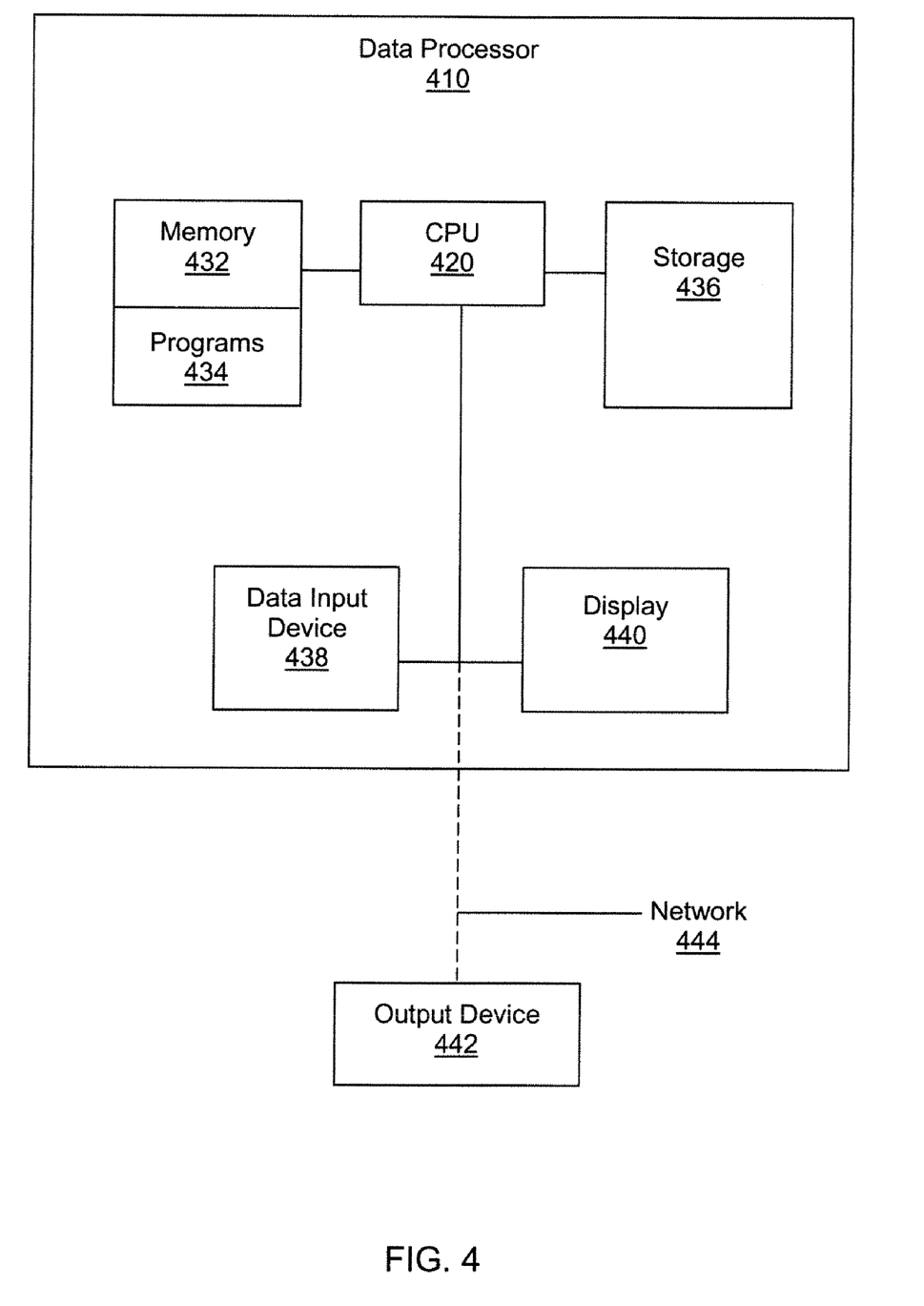
FIG. 4 illustrates an exemplary data processing system operable to enhance the visibility of a medical device as shown on a display.

The method for enhancing the visibility of medical devices may be facilitated by a data processing system. FIG. 4 is a block diagram of an exemplary data processor 410 configured or adapted to provide functionality for enhancing the visibility of medical devices. The data processor 410 may include a central processing unit (CPU) 420, a memory 432, a storage device 436, a data input device 438, and a display 440. The data processor 410 also may have an external output device 442, which may be a display, a monitor, a printer or a communications port. The data processor 410 may be a personal computer, work station, server, part of the imaging system, or other system. The data processor 410 may be interconnected to a network 444, such as an intranet, the Internet, or an intranet connected to the Internet. The data processor 410 may be interconnected to another location via the network 444 either by data lines or by wireless communication. The data processor 410 is provided for descriptive purposes and is not intended to limit the scope of the present system. The data processor may have additional, fewer, or alternate components.

A program 434 may reside on the memory 432, storage device 436, or another memory (e.g., hard drive removable media, RAM, or network buffer). The program 434 may include one or more sequences of executable code or coded instructions that are executed by the CPU 420. The program 434 may be loaded into the memory 432 from the storage device 436 or network or removable media. The CPU 420 may execute one or more sequences of instructions of the program 434 to process data. The program 434 may provide functionality as discussed herein.

Image, patient, and model related data may be entered via the data input device 438 or another input device, or received via the network 444 or other network. The data processor 410 may receive and store image, patient, and model related data received in the memory 432, the storage device 436, or other storage unit. The program 434 may direct that the data received be stored on or read from machine-readable medium, including secondary storage devices such as hard disks, floppy disks, CD-ROMS, and DVDs; electromagnetic signals; or other forms of machine readable medium, either currently known or later developed.

The program 434 may instruct the data processor 410 to depict the image, patient, and/or model related information in one or more windows on the display 440, the external output device 442, or other display screen. The image, patient, and/or model related information may be depicted visually or textually. The data processor 410 may retrieve the image, patient, and/or model data from machine-readable medium, including secondary storage devices such as hard disks, floppy disks, CD-ROMS, and DVDs; electromagnetic signals; or other forms of machine readable medium, either currently known or later developed.

The program 434 may direct the data processor 410 to scroll through image, patient, and/or model related information. The data processor 410 may divide the display 440, output device 442, or other display screen into multiple virtual sub-regions. Each of the virtual sub-regions may be associated with a specific image, patient, and/or model. For instance, the display may be split into four quadrants. Other sub-regions may be provided.

The data processor 410 may direct the display of image, patient, and/or model data on the display 440, output device 442, or other display screen. The data processor 410 also may direct the display of icons on the display 440, output device 442, or other display screen. The display 440, output device 442, or other display screen may be a touch screen, a touch pad, a haptic device, or other vibrational or physical feedback device.

The user interface may accept one or more operations performed on the display. For instance, the user interface may provide for the selection of an area of interest within an image, such as after the user moves a cursor via an input device or touches a portion of a touch screen. Other operations may be performed While the invention has been described above by reference to various embodiments, it should be understood that many changes and modifications can be made without departing from the scope of the invention. The description and illustrations are by way of example only. Many more embodiments and implementations are possible within the scope of this invention and will be apparent to those of ordinary skill in the art. The various embodiments are not limited to the described environments and have a wide variety of applications.

It is intended in the appended claims to cover all such changes and modifications which fall within the true spirit and scope of the invention. Therefore, the invention is not limited to the specific details, representative embodiments, and illustrated examples in this description. Accordingly, the invention is not to be restricted except in light as necessitated by the accompanying claims and their equivalents.

The invention claimed is:

1. A method of automatic image enhancement, the method comprising:
    using at least one computer system for,
        acquiring an image of an implanted medical device internal to a patient;
        identifying the type of medical device in the image and selecting the medical device from model data of a plurality of predetermined stored different types of medical device as having a best fit and in response to at least one of,
            (a) user selection command selecting between said plurality of different types of medical device and
            (b) analysis of said image of said medical device;
        determining model data associated with the identified and selected medical device based upon the identification of the medical device type; and
        enhancing visibility of the medical device as shown in the image as a function of model data associated with the medical device by using the model data to enhance visibility of the medical device by automatically fitting the model data to the medical device as shown in the image using geometric parameters comprising at least one of, length, width and position.

2. The method of claim 1, wherein
said medical device comprises an implanted therapeutic medical device of said patient and said model data geometric parameters of said medical device comprise at least one of, position of struts, and non-expanded or expanded status of a stent.

3. A method of automatic image enhancement, the method comprising:
    using at least one computer system for,
        acquiring an image of a medical device internal to a patient comprising an implanted therapeutic medical device of said patient;
        identifying the type of medical device in the image from a plurality of different types of medical device in response to at least one of,
            (a) user selection command selecting between said plurality of different types of medical device and
            (b) analysis of said image of said medical device;
        determining model data associated with the medical device based upon the identification of the medical device type, said model data comprises geometric parameters of said medical device; and
        enhancing visibility of the medical device as shown in the image as a function of model data associated with the medical device by using the model data to enhance visibility of the medical device using a best fit algorithm to fit the model data onto the medical device as shown in the image and said geometric parameters comprise at least one of, length, width, position of struts, and non-expanded or expanded status of a stent.

4. The method of claim 1, including identifying the position of the medical device within the image wherein using the model data to enhance visibility of the medical device includes redrawing the model data to fit the medical device as shown in the image.

5. The method of claim 4, wherein redrawing the model data includes rotating or translating the model data to match at least a portion of the image associated with the medical device.

6. The method of claim 4, wherein redrawing the model data includes resizing the model data to match at least a portion of the image associated with the medical device.

7. The method of claim 1, wherein the image is acquired using a C-arm imaging device.

8. The method of claim 1, the method comprising using organ model data to alter the image, the organ model data associated with a model of at least a portion of a heart.

9. A method of automatic image enhancement, the method comprising:
    employing at least one computer system for,
        identifying a type of implanted therapeutic medical device and selecting the medical device from model data of a plurality of predetermined stored different types of medical device as having a best fit and in response to at least one of,
            (a) user selection command selecting between said plurality of different types of medical device and
            (b) analysis of an image of said medical device;
        acquiring model data associated with the identified and selected medical device based upon the identification of the medical device type;
        acquiring an image of the medical device within a patient; and
        enhancing visibility of the medical device as shown in the image as a function of the model data to alter a display of the image by using the model data to enhance visibility of the medical device by automatically fitting the model data to the medical device as shown in the image using geometric parameters comprising at least one of, length, width and position.

10. The method of claim 9, the method comprising:
acquiring organ model data that models a bodily structure shown in the image; and
using the organ model data to alter the display of the image such that visibility of the bodily structure as shown in the image is enhanced.

11. The method of claim 9, wherein an image of the medical device is acquired using a bi-planar imaging device.

12. The method of claim 9, wherein-an image of the medical device is generated from a plurality of x-ray images of the medical device taken at different angles.

13. The method of claim 9, wherein a virtual medical device represented by the model data is adjusted to fit onto the medical device as shown in the image and then the adjusted virtual medical device is superimposed onto the medical device as shown in an image of the medical device.

14. The method of claim 13, wherein the virtual medical device is bent to align with the medical device as shown in an image of the medical device.

15. The method of claim 13, wherein the virtual medical device is rotated or resized to align with the medical device as shown in an image of the medical device.

16. The method of claim 9, the method comprising accepting a user input that identifies a localized area of an image of the medical device that shows the medical device.

17. A data processing system for automatic image enhancement, the system comprising:
    at least one computer system including,
        means for acquiring an image of an implanted medical device within a patient;
        means for identifying the type of medical device in the image and selecting the medical device from model data of a plurality of predetermined stored different types of medical device as having a best fit and in response to at least one of,
            (a) user selection command selecting between said plurality of different types of medical device and
            (b) analysis of said image of said medical device;
        means for determining model data associated with the identified and selected medical device based upon the identification of the medical device type; and
        a processor operable to alter a display of the image based upon an identification of the medical device such that visibility of the medical device as shown on the display is enhanced by using the model data to enhance visibility of the medical device by automatically fitting the model data to the medical device as shown in the image using geometric parameters comprising at least one of, length, width and position.

18. The data processing system of claim 17, wherein the processor is operable to perform operations on model data associated with the medical device to align a virtual medical device with the medical device as shown on the display.

19. The data processing system of claim 17, wherein the processor is operable to resize or rotate a virtual medical device onto the medical device as shown on the display.

20. The data processing system of claim 17, wherein the processor is operable accept a user input identifying a localized portion of the image in which the medical device is displayed and alter the localized portion identified to enhance visibility of the medical device.

21. A non-transitory computer-readable medium having instructions thereon executable on a computer, the instructions comprising:
    acquiring an image of a medical device internal to a patient;
        identifying the type of medical device in the image and selecting the medical device from model data of a plurality of predetermined stored different types of medical device as having a best fit and in response to at least one of,
            (a) user selection command selecting between said plurality of different types of medical device and
            (b) analysis of said image of said medical device;
        determining model data associated with the identified and selected medical device based upon the identification of the medical device type; and
        fitting a virtual medical device onto a corresponding actual medical device shown in an internal image of the actual medical device by using the model data to enhance visibility of the medical device by automatically fitting the model data to the medical device as shown in the image using geometric parameters comprising at least one of, length, width and position; and
        increasing visibility of the actual medical device as shown on a display.

22. The computer-readable medium of claim 21, wherein the virtual medical device is fitted onto the actual medical device using a best fit algorithm.

23. The computer-readable medium of claim 21, the instructions comprising:
    said medical device comprises an implanted therapeutic medical device of said patient and said model data geometric parameters of said medical device comprise at least one of position of struts, and non-expanded or expanded status of a stent.

24. The computer-readable medium of claim 23, wherein the medical device is a stent and the identification includes whether the stent is expanded or un-expanded.

* * * * *